US010945653B2

(12) United States Patent
Davie et al.

(10) Patent No.: US 10,945,653 B2
(45) Date of Patent: Mar. 16, 2021

(54) SURFACE ELECTROMYOGRAPHY SYSTEM, RECORDER AND METHOD

(71) Applicant: KONINKLIJKE PHILIPS N.V., Eindhoven (NL)

(72) Inventors: Alan James Davie, Cambridge (GB); Sandrine Magali Laure Devot, Aachen (DE); Rene Martinus Maria Derkx, Eindhoven (NL); Jakob Van De Laar, Oosterhout (NL)

(73) Assignee: Koninklijke Philips N.V., Eindhoven (NL)

( * ) Notice: Subject to any disclaimer, the term of this patent is extended or adjusted under 35 U.S.C. 154(b) by 419 days.

(21) Appl. No.: 15/580,709

(22) PCT Filed: May 31, 2016

(86) PCT No.: PCT/EP2016/062297
§ 371 (c)(1),
(2) Date: Dec. 8, 2017

(87) PCT Pub. No.: WO2016/198288
PCT Pub. Date: Dec. 15, 2016

(65) Prior Publication Data
US 2018/0184938 A1      Jul. 5, 2018

(30) Foreign Application Priority Data
Jun. 12, 2015  (EP) .................................... 15171932

(51) Int. Cl.
*A61B 5/00* (2006.01)
*A61B 5/296* (2021.01)
*A61B 5/08* (2006.01)

(52) U.S. Cl.
CPC ................. *A61B 5/296* (2021.01); *A61B 5/08* (2013.01); *A61B 5/6823* (2013.01); *A61B 5/7221* (2013.01)

(58) Field of Classification Search
CPC ... A61B 5/0488; A61B 5/0024; A61B 5/0492; A61B 5/0816; A61B 5/11; A61B 5/0408;
(Continued)

(56) References Cited

U.S. PATENT DOCUMENTS

| 4,890,630 | A | * | 1/1990 | Kroll | .................. | A61B 5/04085 |
| | | | | | | 128/902 |
| 5,549,656 | A | * | 8/1996 | Reiss | ................. | A61N 1/36003 |
| | | | | | | 600/546 |

(Continued)

FOREIGN PATENT DOCUMENTS

| CN | 103393420 A | 11/2013 |
| CN | 104665822 B | 1/2015 |

(Continued)

*Primary Examiner* — May A Abouelela
(74) *Attorney, Agent, or Firm* — Daniel H. Brean (57) ABSTRACT

The present invention relates to determining a neural respiratory drive (NRD) in patients with chronic obstructive pulmonary disease (COPD) based on surface electromyography measurements taken from the intercostal muscles on the chest of a subject (100). An electromyography system is presented that comprises a first electrode (2') and a second electrode (3') for contacting a skin of a subject (100), and a recorder (4') for recording an electromyogram between the first electrode (2') and the second electrode (3'); wherein the first electrode (2') comprises a first electrode area (2A) and a second electrode area (2B) for contacting the skin of the subject (100), wherein the first electrode area (2A) and the second electrode area (2B) are insulated from each other; and the recorder (4') is configured to form a noise measurement between the first electrode area (2A) and the second electrode area (2B) of the first electrode (2') for determining
(Continued)

a contact quality of an electrode-skin contact of the first electrode (2'). According to further aspects, a corresponding electromyogram recorder (4') for an electromyography system, a method for electromyogram measurements and a corresponding computer program are presented.

13 Claims, 7 Drawing Sheets

(58) Field of Classification Search
CPC .............. A61N 1/0456; A61N 1/36021; A61N 1/36071; A61N 1/36135; A61N 1/0476
USPC .......................................... 600/300, 546, 372
See application file for complete search history.

(56) References Cited

U.S. PATENT DOCUMENTS

| | | | | |
|---|---|---|---|---|
| 5,679,004 A * | 10/1997 | McGowan | .............. | A63B 69/00 434/247 |
| 5,685,316 A | 11/1997 | Beliaev et al. | | |
| 5,711,307 A * | 1/1998 | Smits | .................... | A61B 5/0488 600/546 |
| 6,047,202 A * | 4/2000 | Finneran | .............. | A61B 5/0492 600/382 |
| 6,076,011 A * | 6/2000 | Hoover | ................ | A61B 5/0488 600/546 |
| 6,289,245 B1 * | 9/2001 | Mo | .................... | A61B 5/04882 600/546 |
| 6,643,541 B2 * | 11/2003 | Mok | .................... | A61B 5/0002 128/903 |
| 7,797,039 B2 * | 9/2010 | Koivumaa | ........... | A61B 5/0408 128/901 |
| 8,281,787 B2 | 10/2012 | Burton | | |
| 8,738,122 B2 * | 5/2014 | Liu | ........................ | G06F 3/015 434/247 |
| 8,825,128 B2 | 9/2014 | Ylostalo et al. | | |
| 8,855,753 B2 * | 10/2014 | Kim | .................... | A61B 5/0408 600/509 |
| 9,289,178 B2 | 3/2016 | Kim et al. | | |
| 9,888,971 B2 | 2/2018 | Taylor | | |
| 9,931,050 B2 | 4/2018 | Kaib | | |
| 10,194,869 B2 * | 2/2019 | Kim | .................... | A61B 5/7214 |
| 2003/0125636 A1 * | 7/2003 | Jeong | .................... | A61B 5/0488 600/546 |
| 2003/0171661 A1 * | 9/2003 | Tong | .................. | A61B 5/04004 600/300 |
| 2004/0054273 A1 * | 3/2004 | Finneran | .............. | A61B 5/04004 600/393 |
| 2006/0079801 A1 * | 4/2006 | DeLuca | .............. | A61B 5/04004 600/546 |
| 2006/0129057 A1 * | 6/2006 | Maekawa | .................. | A61B 5/0488 600/546 |
| 2006/0173364 A1 * | 8/2006 | Clancy | .................... | A61B 5/04 600/485 |
| 2006/0189882 A1 * | 8/2006 | Thomas | .............. | A61B 5/04882 600/546 |
| 2007/0167859 A1 * | 7/2007 | Finneran | ............... | A61B 5/0492 600/546 |
| 2009/0036792 A1 * | 2/2009 | DeLuca | ................ | A61B 5/0492 600/546 |
| 2009/0209878 A1 * | 8/2009 | Sanger | .................. | A61B 5/0488 600/546 |
| 2009/0326406 A1 | 12/2009 | Tan et al. | | |
| 2011/0028823 A1 | 2/2011 | De Luca et al. | | |
| 2011/0077497 A1 * | 3/2011 | Oster | .................... | A61B 5/0002 600/372 |
| 2011/0118581 A1 * | 5/2011 | Jadidi | .................. | A61B 5/0492 600/372 |
| 2011/0237904 A1 * | 9/2011 | Kim | ...................... | A61B 5/0402 600/300 |
| 2011/0288605 A1 * | 11/2011 | Kaib | ...................... | A61B 5/021 607/5 |
| 2011/0306892 A1 * | 12/2011 | Kim | ...................... | A61B 5/0408 600/509 |
| 2012/0150010 A1 * | 6/2012 | Hayes-Gill | ........ | A61B 5/02411 600/382 |
| 2012/0209134 A1 * | 8/2012 | Morita | ............... | A61B 5/04012 600/546 |
| 2012/0235499 A1 * | 9/2012 | Liu | ........................ | H02J 7/025 307/104 |
| 2012/0238894 A1 * | 9/2012 | Principe | .............. | A61B 5/04882 600/546 |
| 2012/0310069 A1 | 12/2012 | Clare et al. | | |
| 2013/0237795 A1 | 9/2013 | Carr | | |
| 2014/0088394 A1 | 3/2014 | Sunderland | | |
| 2014/0257128 A1 | 9/2014 | Moxon et al. | | |
| 2014/0257129 A1 | 9/2014 | Choi et al. | | |
| 2015/0025330 A1 | 1/2015 | Alpert | | |
| 2015/0065813 A1 * | 3/2015 | Wochlik | .............. | A61B 5/04845 600/301 |
| 2015/0164427 A1 * | 6/2015 | Volpe | .................... | A61B 5/0205 600/388 |
| 2016/0135743 A1 * | 5/2016 | Cobbett | .............. | B29C 66/4324 600/479 |
| 2016/0150987 A1 * | 6/2016 | Kwon | ................ | A61B 5/04012 600/476 |
| 2016/0278663 A1 * | 9/2016 | Freeman | ................ | A61B 7/005 |
| 2017/0143272 A1 * | 5/2017 | Brouse | .............. | A61B 5/02416 |
| 2017/0231521 A1 * | 8/2017 | Axelrod | .............. | A61B 5/04017 600/546 |

FOREIGN PATENT DOCUMENTS

| | | |
|---|---|---|
| EP | 2394571 A1 | 12/2011 |
| JP | 2001231761 A | 8/2001 |
| JP | 2007159722 A | 6/2007 |
| JP | 2013121489 A | 6/2013 |
| WO | 2008005478 A2 | 1/2008 |
| WO | 2013045920 A1 | 4/2013 |

\* cited by examiner

SURFACE ELECTROMYOGRAPHY SYSTEM, RECORDER AND METHOD

CROSS-REFERENCE TO PRIOR APPLICATIONS

This application is the U.S. National Phase application under 35 U.S.C. § 371 of International Application Serial No. PCT/EP2016/062297, filed on 31 May 2016, which claims the benefit of European Application No. 15171932.5, filed on 12 Jun. 2015. These applications are hereby incorporated by reference herein.

FIELD OF THE INVENTION

The field of the present invention relates to determining a neural respiratory drive (NRD) in patients with chronic obstructive pulmonary disease (COPD) based on surface electromyography measurements taken from the intercostal muscles on the chest of a subject. The present invention relates to surface electromyography and in particular to a surface electromyography system and corresponding recorder and method as well as to a corresponding computer program for carrying out said method.

BACKGROUND OF THE INVENTION

Electromyography (EMG) is a technique for determining an activity of a muscle. An electromyography system detects an electrical potential generated by muscle cells when these cells are electrically or neurologically activated. One or more electrodes are applied to obtain a voltage signal indicative of an activity of the muscle.

Signals can either be measured directly within the muscle (invasive EMG) or on the skin above the muscle (surface EMG). For invasive EMG, an electrode is directly inserted into the muscle tissue of interest. For surface EMG, as a non-invasive technique, an electrode is applied to the skin of the subject.

Surface EMG measurements involve the detection, processing and recording of very small electrical variations generated by muscle tissue. These signals are often only a few microvolts in amplitude and can therefore be subject to interference from other more dominant noise sources, either from the measurement system or from the human body itself.

One application of surface EMG is determining a neural respiratory drive (NRD) in patients with chronic obstructive pulmonary disease (COPD). An NRD value may be calculated using electromyography measurements taken from the intercostal muscles on the chest of the subject.

WO 2013/045920 A1 discloses a corresponding patient monitoring method and monitoring device. A neural respiratory drive (NRD) is measured by obtaining a measure of the second intercostal space parasternal electromyogram. Signals are acquired using conventional electrodes and amplifiers. The signals are processed using analog-to-digital conversion followed by digital filtering and arithmetic conversion of the signal. For improving the EMG signal it is suggested to apply a filtering algorithm to remove electrocardiogram (ECG) artifacts from the EMG signal. A high pass filter is applied to the raw signal to remove baseline noise and additional band pass filtering between 12-20 Hz can be performed to remove respiration artifacts. A signal quality of the measured EMG signal is determined based on a comparison of detectable respiratory activity and background noise level in the measured EMG signal.

US 2014/0088394 A1 discloses an electromyography instrument which evaluates the quality of the connections made between the electrodes and the body. The quality is measured as an electrical impedance, where a higher impedance indicates a lower quality connection and a lower impedance indicates a higher quality connection.

WO 2008/005478 A2 relates to the treatment of neurological disorders via electrical stimulation and methods related thereto. Also in this disclosure, an impedance can be determined and used as a measure of the quality of the electrodes' electrical contact to the skin.

The placement of surface EMG electrodes is typically left to trained professionals. The placement of surface EMG electrodes can involve preparation of the skin where the EMG electrodes are to be placed. Such preparation can involve cleaning, shaving and abrasion of a topmost skin layer to remove dead skin cells. Nonetheless, significant intra-individual measurement variability can result from inconsistent electrode attachment.

SUMMARY OF THE INVENTION

It is an object of the present invention to facilitate the handling of an electromyography system. In particular, it would be advantageous to detect a poor quality contact between an electrode and the skin such that even an untrained person can take reliable measurements. It is also an object of the present invention to provide a corresponding method as well as a corresponding computer program.

According to a first aspect of the present invention, an electromyography system is presented that comprises:
- a first electrode and a second electrode for contacting a skin of a subject, and
- a recorder for recording an electromyogram between the first electrode and the second electrode; wherein
- the first electrode comprises a first electrode area and a second electrode area for contacting the skin of the subject, wherein the first electrode area and the second electrode area are insulated from each other; and wherein
- the recorder is configured to perform a noise measurement between the first electrode area and the second electrode area of the first electrode for determining a contact quality of an electrode-skin contact of the first electrode.

In a further aspect of the present invention a method for electromyogram measurements is provided. The method comprises the steps of:
- obtaining a first signal from a first electrode area of a first electrode for contacting a skin of a subject;
- obtaining a second signal from a second electrode area of the first electrode, wherein the first electrode area and the second electrode area are insulated from each other;
- performing a noise measurement between the first electrode area and the second electrode area of the first electrode for determining a contact quality of an electrode-skin contact of the first electrode; and
- recording an electromyography signal between the first electrode and a second electrode.

According to yet another aspect of the present invention, an electromyogram recorder for an electromyography system as described above is presented for recording an electromyography signal between a first electrode and a second electrode, the recorder comprising:
- a first interface for obtaining a first signal from a first electrode area of the first electrode for contacting a skin of a subject;

a second interface for obtaining a second signal from a second electrode area of the first electrode, wherein the first electrode area and the second electrode area are insulated from each other;

wherein the recorder is configured to perform a noise measurement between the first electrode area and the second electrode area of the first electrode for determining a contact quality of an electrode-skin contact of the first electrode.

In further aspects of the present invention, there are provided a computer program which comprises program code means for causing a computer to perform the steps of the method disclosed herein when said computer program is carried out on a computer, as well as an non-transitory computer-readable recording medium that stores therein a computer program product, which, when executed by a processor, causes the method disclosed herein to be performed.

Preferred embodiments of the invention are defined in the dependent claims. It shall be understood that the claimed method, electromyogram recorder and computer program can have similar and/or identical preferred embodiments as the claimed electromyography system and as defined in the dependent claims.

The herein presented solutions provide a possibility to facilitate the handling of an electromyography system. In particular, aspects of the proposed solutions provide a possibility to detect a poor quality contact between an electrode and the skin such that even an untrained person can take reliable measurements.

The present invention suggests separating the actual EMG measurement form determining the contact quality of an electrode-skin contact of an individual electrode. While the actual EMG measurement is performed between the first electrode and the second electrode, it is suggested that the first electrode comprises a first electrode area and a second electrode area for contacting the skin of the subject respectively, wherein the first electrode area and the second electrode area are insulated from each other. In other words, it is suggested to subdivide the first electrode into a first and a second area and to perform a noise measurement between the first electrode area and the second electrode area of the first electrode for determining an electrode-skin contact quality. Hence, instead of determining an overall EMG signal quality, the contact quality of individual electrode skin contacts can be determined. An advantage of performing a noise measurement is that it can be performed as a passive measurement and does not require injecting signals into the body of the subject as would be, for example, required for an impedance measurement. Hence, the admission of an electromyography system for home use and approval by authorities may be facilitated since no signals have to be injected into the body of the subject. Since the device is passive the regulations may be less stringent. The proposed electromyography can be particularly well-suited for hospital as well as home settings. Advantageously, the proposed electromyography system enables improved repeatability and accuracy of neural respiratory drive (NRD) value determination via EMG. A further advantage of not having signals injected into the body can be that for an embodiment that uses 'continuous' EMG recording over a long period of time, there may be less interference to the wanted EMG signal.

It should be noted that noise in EMG measurements can come from a number of sources. Such noise sources can include contributions of thermal (Johnson) noise, measurement system noise, a metal-electrolyte interface, the electrode-skin interface, and EMG signals or crosstalk from other muscles. In surface EMG measurements for determining an activity of the intercostal muscles, intermittent interference caused by electrical signals of the heart can be one of the most significant sources of crosstalk. It has been found that the metal-electrolyte noise, e.g. metal-gel noise in a wet-gel electrode, can be neglected. It has further been found that EMG noise or crosstalk from more distant muscles tends to be correlated at the first and second electrode area and can thus be at least partially rejected as common mode noise. The inventors have found that a significant amount of interference in surface EMG measurements can be attributed to the noise generated in the boundary between the measuring electrodes and the skin, in particular an electrolyte of the electrode and the skin. It was found that this noise usually has a 1/f spectral characteristic. In particular, a power spectrum of noise from electrodes on the skin can have a $1/f\alpha$ characteristic, where a is between 1.5 and 2. This noise source can be explained as a result of ionic charge transport through a semi-porous membrane, i.e., through the skin-electrolyte boundary in this case. An amount and repeatability of excess noise occurring in this way can be highly dependent upon the quality of the electrode-skin contact.

By measuring the noise between the first and second area of the first electrode, the electrode-skin contact of the first electrode area for contacting the skin of the subject and the electrode-skin contact of the second electrode area for contacting the skin of the subject can be seen as two noise sources that are connected in series. Based on such a series measurement, a noise contribution of the individual electrode-skin contacts of the first and second area of the first electrode can be determined or estimated. Correspondingly a noise contribution of a parallel combination of first and second area of the first electrode can be determined or estimated, for example, for a subsequent EMG measurement using a combination, in particular a parallel connection, of both electrodes areas. This will be explained in more detail for an example with reference to the figures.

As used herein, contacting a skin of the subject can refer to electrically contacting the skin of the subject, in particular establishing a contact which enables an EMG measurement.

As used herein an electrode area can refer to a contact area for contacting a skin of the subject. The first electrode can comprise two or more electrode areas for contacting the skin of the subject. The electromyography system can comprise two or more electrodes and at least one of the electrodes comprises at least two electrode areas for contacting the skin of the subject.

As used herein, a signal from an electrode area can refer to a signal indicative of an electric potential at an electrode area.

In an embodiment, similar to the first electrode, the second electrode comprises a third electrode area and a fourth electrode area for contacting the skin of the subject, wherein the third electrode area and the fourth electrode area are insulated from each other; and the recorder is further configured to also perform a noise measurement between the third electrode area and the fourth electrode area of the second electrode for determining a contact quality of an electrode-skin contact of the second electrode. Thereby, the electrode-skin contact of the second electrode can be determined based on a noise measurement of the two electrically insulated areas comprised in the second electrode. An advantage of this embodiment is that an electrode-skin contact can be determined separately for the first electrode and for the second electrode. Optionally, the contact quality of one or more of the electrodes is indicated to the user by the system. Hence, assuming that one of the two electrodes has already been positioned correctly, the system may indicate which one of the two electrodes has a poor electrode-skin contact and should be rearranged. Thereby, the handling of the electromyography system is improved.

Correspondingly, in an embodiment, the proposed method can further comprise the steps of obtaining a third signal from a third electrode area of a second electrode for contacting a skin of a subject; obtaining a fourth signal from a fourth electrode area of the second electrode, wherein the third electrode area and the fourth electrode area are insulated from each other; and determining a surface contact quality of an electrode-skin contact of the second electrode based on a noise measurement between the third electrode area and the fourth electrode area of the second electrode.

In an embodiment, the electromyography system further comprises a switching unit for selectively connecting
the first electrode area and the second electrode area to a measurement unit of the recorder for performing the noise measurement; or
the first electrode and the second electrode to the measurement unit of the recorder for recording the electromyogram. Optionally, the switching unit is further configured for selectively connecting a third electrode area and a fourth electrode area of the second electrode to a measurement unit of the recorder for performing a noise measurement. Hence, a second noise measurement can performed between the third electrode area and the fourth electrode area of the second electrode for determining a contact quality of an electrode-skin contact of the second electrode. An advantage of this embodiment is that a measurement unit of the recorder can be used to perform both the one or more noise measurements and the actual recording of the electromyogram. It should be noted, that a switching unit can be arranged at different stages of a signal processing chain for processing signals received from the electrodes or electrode areas respectively. For example, a switching unit can be arranged directly at an electrode, at connection points or leads from the first electrode area and the second electrode area respectively, before or inside of the recorder. Hence, the recorder can comprise the switching unit. The switching unit could be applied after an initial amplifier, filter and/or analogue to digital converter.

In an embodiment, the electromyography system further comprises a combiner unit for combining signals from the first electrode area and the second electrode area to obtain a combined signal of the first electrode. In other words, even though the first electrode comprises a first electrode area and an electrically insulated second electrode area, which are advantageously used for the noise measurement, the first electrode area and the second electrode area can be coupled together by the combiner unit for the actual recording of the electromyogram between the first electrode and the second electrode. In other words if can be preferred to short-circuit the first and second electrode areas in particular for reducing an effect of possibly unequal noise sources for the electrode areas within a single patch or electrode. A corresponding combiner unit can also be used for combining signals from the third electrode area and the fourth electrode area to obtain a combined signal of the second electrode. The signals can be combined, for example, electrically or can also be combined after analog-to-digital conversion in the digital domain. An advantage of combining the first electrode area and the second electrode area for recording the electromyogram is that a larger area electrode can provide at least one of a better contact, lower impedance and less noise. It has been found that the noise is proportional to $1/\sqrt{electrodearea}$. Preferably, the combiner unit is an electric or electronic switching device. The recorder can comprise the combiner. Preferably, signal leads coming from the first electrode area and the second electrode area are not mechanically manipulated between a measurement for determining the contact quality of the electrode-skin contact and an actual EMG measurement, such that the electrode-skin contact is not changed.

In an embodiment, the recorder is configured to determine a noise contribution of the first electrode based on the noise measurement between the first electrode area and the second electrode area of the first electrode. In other words, a noise contribution or estimated noise contribution of the entire first electrode can be determined based on the previous series measurement between the first electrode area and the second electrode area of the first electrode. In other words, a total noise contribution of the electrode skin contact of the first electrode can be determined. This total noise contribution then represents the noise of the electrode-skin contact of the first electrode for parallel use of the first electrode area and the second electrode area.

In an embodiment the first electrode is comprised in an electrode patch comprising the first electrode area and the second electrode area. An advantage of this embodiment is that such an electrode patch comprising the first electrode area and the second electrode area can be handled as already known from conventional single-contact electrodes. A first electrode patch comprising the first electrode area and a second electrode area and a separate second electrode patch comprising the third electrode area and the fourth electrode area of the second electrode can be applied without substantially changing existing procedures. It will be appreciated that respective separate connections between the respective electrode areas and the recorder of the electromyography system can be established.

In an embodiment, the first electrode comprises
a first connection point electrically coupled to the first electrode area; and
a second connection point electrically coupled to the second electrode area. Hence, separate connections of the two electrode areas of one electrode are provided. The two separate electrode areas can be connected for example to the recorder of the electromyography system via two separate leads. It will be appreciated, that separate cables could be used or one cable comprising connectors for connection to the first and second connection point of the first electrode. The recorder can comprise respective interfaces for connection to the respective connection points of each electrode.

In an embodiment at least one of the electrodes is a wet-gel electrode and/or at least one of the electrode areas is a wet-gel electrode area. At least one of the electrodes can be a silver/silver-chloride electrode and/or at least one of the electrode areas can be a silver/silver-chloride electrode area. An advantage of these embodiments is that an electrode and/or electrode area can be implemented using reliable techniques which can advantageously be manufactured at low cost.

In an embodiment, the first electrode area and the second electrode area are separated by distance of 3 to 4 mm. An advantage of this separation is that a reliable noise measurement between the first electrode area and the second electrode area can be performed. It has been found that the farther the electrode areas are spaced apart on a muscle, the larger a signal from an underlying muscle. However for the proposed noise measurement a large signal from the underlying muscle is not desirable. Moreover, the farther the electrode areas are spaced apart, the more adjacent muscles could result in crosstalk. The proposed separation is particularly advantageous, since the first electrode area and the second electrode area are spaced sufficiently close to each other such that the target signal of the muscle to be measured in the electromyogram and also noise in form of cross talk from other muscles only have a low amplitude. At the same time, the spacing is sufficiently wide, that electric insulation between the first electrode area and the second electrode area can be ensured even when applied to the skin of the subject. The first electrode area and the second electrode area of the first electrode can be seen as adjacent or neighboring electrode areas for contacting the skin of the subject respectively. When applied to the skin of the subject, a separation between the first electrode and the second electrode is preferably larger than the separation between first electrode area and the second electrode area of the first electrode.

It was found that EMG signals generated from within the body and measured at the surface via electrodes get smaller in amplitude as the spacing between the electrodes decreases. As a result, the noise measured via the first electrode comprising the first and second electrode areas for contacting the skin of the subject is dominated by the series combination of the two noise sources in the electrode alone, which can therefore serve as an indicator of a contact quality of the electrode-skin contact of the first electrode. Regarding the placement of EMG electrodes, De Luca et al., "Inter-electrode spacing of surface EMG sensors: Reduction of crosstalk contamination during voluntary contractions", Journal of Biomechanics 2011, teach that the farther electrodes are apart on a muscle, the larger the signal. Hence, a large electrode spacing on a muscle would be desirable for obtaining a target muscle signal with a large amplitude. However, the larger the distance, the more adjacent muscles may affect the signal. Hence, the study teaches there is a balance between a desired target signal amplitude and cross talk from other muscles. This scientific study teaches an inter-electrode spacing of 10 mm for reducing cross talk signals.

In an embodiment, the electromyography system further comprises a reference electrode. The ground or reference electrode as an optional additional electrode may be used to limit common mode noise, such as power line noise. As an advantage, the common mode rejection ratio (CMRR) can thereby be improved. A further advantage of the reference electrode can be to limit any common mode signals in the primary measurement electrodes from overloading the EMG recorder input amplifier. Advantageously, the reference electrode is placed on an electrically neutral place on the body such as the clavicle. The reference electrode can be placed far away from the first and the second electrode on an electrically neutral part of the body, i.e., a bony prominence.

In an embodiment, the electromyography system further comprises an output unit for indicating an electrode-skin contact quality. An advantage of this embodiment is that it can be indicated to use it whether an electrode has been attached properly. For example, the user can be warned if a contact quality is above or below a respective predetermined threshold. A contact quality below a predetermined threshold can indicate a poor contact quality. However, a contact quality above a predetermined threshold can indicate that the first electrode area and the second electrode area are not properly separated from one another and may be indicative of the short circuit between those two areas. The output unit can indicate the electrode-skin contact quality using any modality such as providing an acoustic and/or visual message. Furthermore, the user can be instructed to rearrange one or more of the electrodes.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
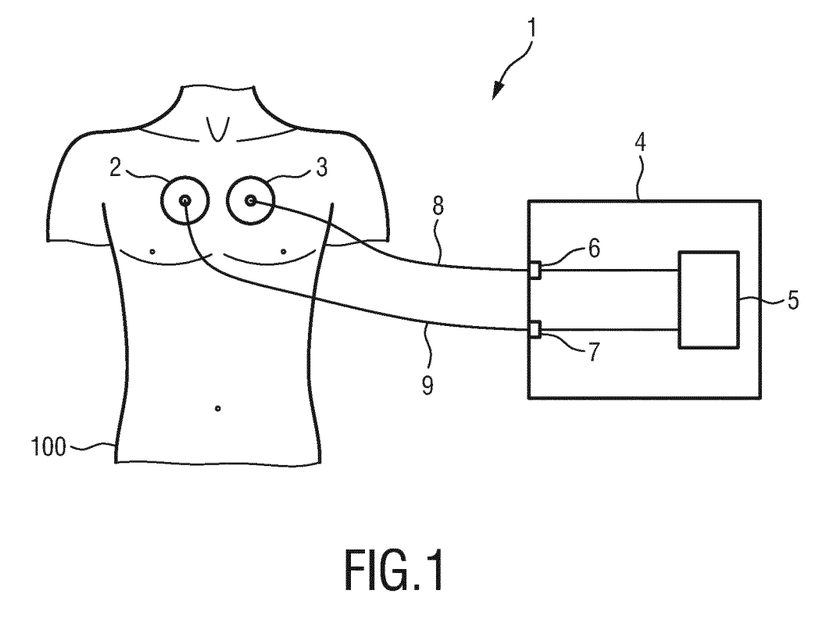
FIG. 1 shows an electromyography system applied to a subject.

FIG. 1 shows an embodiment of an existing electromyography system. The electromyography system is therein denoted in its entirety with reference numeral 1.

The electromyography system 1 comprises a first electrode 2 and a second electrode 3 for contacting a skin of a subject 100 and a recorder 4 for recording an electromyogram between the first electrode 2 and the second electrode 3. The recorder 4 in this embodiment comprises a measurement unit 5 which is connected to a first interface 6 and a second interface 7 of the recorder 4. The first electrode 2 is connected to the first interface 6 of the recorder 4 via a first lead 8 for providing a first signal from the first electrode. The second electrode 3 is connected to the second interface 7 of the recorder 4 via a second lead 9 for providing a second signal from the second electrode 3.

The measurement unit 5 of the recorder 4 can, for example, comprise a differential amplifier for obtaining an electromyogram based on a difference of the first signal obtained from the first electrode 2 and the second signal obtained from the second electrode 3. For example, the recorder 4 can comprise a high gain, high common mode amplifier, an analog-to-digital (A/D) converter and optional data processing and storage capability. The recorder 4 is connected by electrodes to the muscle group to be measured.

Surface EMG measurements involve the detection, processing and recording of very small electrical variations generated by human muscle tissue. The signals are often only a few microvolts in amplitude and are therefore subject to interference from other, more dominant noise sources, either from the measurement system or from the human body itself. A possible application of the EMG system is to measure electrical variations generated by human muscle tissue, i.e. from the intercostal muscles on the chest to calculate an index of neural respiratory drive (NRD) in patients with chronic obstructive pulmonary disease (COPD).

Figure 2:
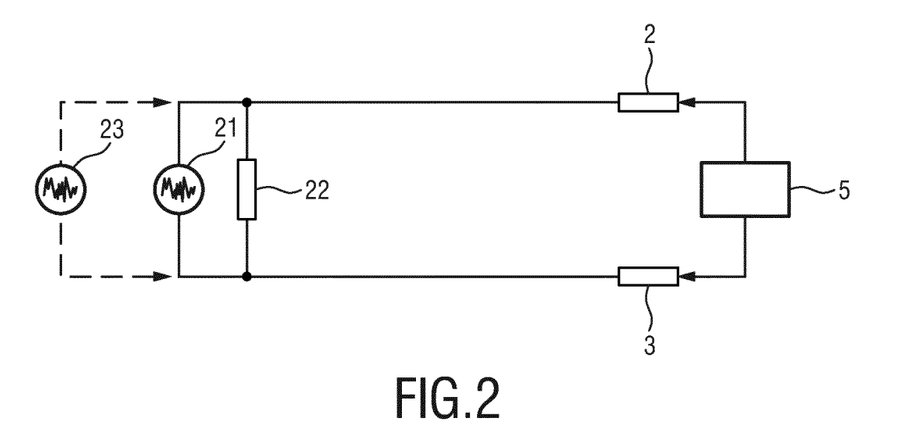
FIG. 2 shows an electrical equivalent model of the EMG setup of FIG. 1.

FIG. 2 shows a simplified electrical equivalent model of the surface EMG measurement setup of FIG. 1. The first electrode 2 and the second electrode 3 are connected to the measurement unit 5 of the recorder 4. In the exemplary embodiment in FIG. 2, the intercostal biopotential signal as the exemplary wanted signal is indicated with reference numeral 11. In addition to the wanted intercostal biopotential signal 21, the electrical equivalent model of FIG. 2 further shows a tissue impedance 22 between the first measurement electrode 2 and the second measurement electrode 3. Furthermore there can be crosstalk, as indicated by crosstalk signal 23, which can be due to unwanted tonic muscle activity or biopotential and/or motion artifacts. Such unwanted contributions are indicated in FIG. 2 by dashed arrows. When performing a measurement via the contacts provided by the first electrode 2 and the second electrode 3 using the measurement unit 5, the measurement unit 5 inevitably sees all signal and noise sources and receives one common signal. A problem involved is that the signal sources and noise sources may look substantially similar in character, which can make it difficult to isolate the individual contributions. Hence, in the setup as shown in FIG. 1, an overall quality of an acquired EMG measurement can be determined for example by determining an overall signal to noise ratio.

Figure 3:
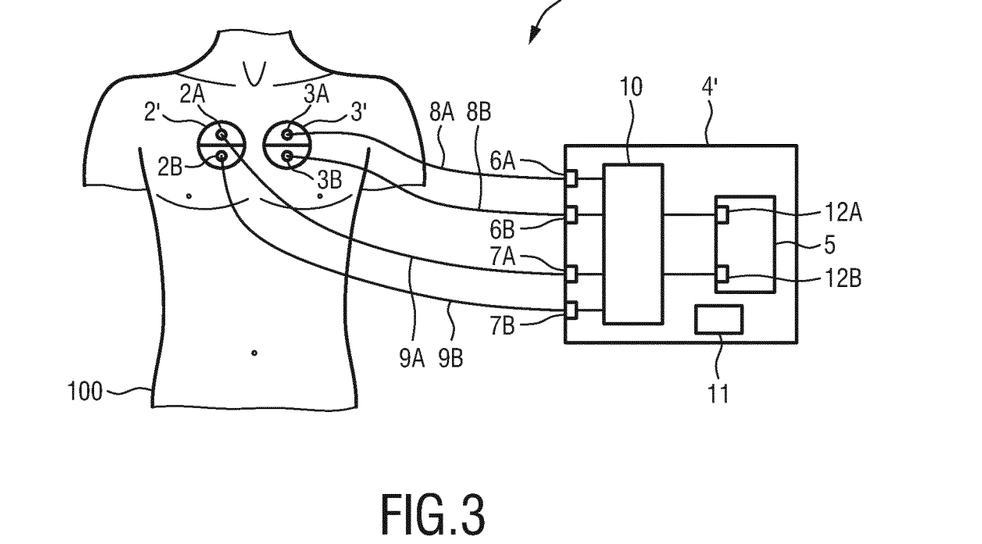
FIG. 3 shows an electromyography system according to an aspect of the present invention applied to a subject.

FIG. 3 shows an embodiment of an electromyography system 1' according to an aspect of the present invention. The electromyography system 1' comprises a first electrode 2' and a second electrode 3' for contacting a skin of a subject 100 and a recorder 4' for recording an electromyogram between the first electrode 2' and the second electrode 3'. The first electrode 2' comprises a first electrode area 2A and a second electrode area 2B for contacting the skin of the subject 100, wherein the first electrode area 2A and the second electrode area 2B are insulated from each other. The second electrode 3' comprises a third electrode area 3A and a fourth electrode area 3B for contacting the skin of the subject 100, wherein the third electrode area 3A and the fourth electrode area 3B are insulated from each other.

The recorder 4' is configured to perform a noise measurement between the first electrode area 2A and the second electrode area 2B of the first electrode 2' for determining a contact quality of an electrode-skin contact of the first electrode 2'. Correspondingly, the recorder 4' can be further configured to also perform a noise measurement between the third electrode area 3A and the fourth electrode area 3B of the second electrode 3' for determining a contact quality of an electrode-skin contact of the second electrode 3'.

In this exemplary embodiment, the recorder 4' comprises a measurement unit 5 and an optional switching unit 10. The switching unit 10 in this embodiment comprises four inputs connected to four interfaces 6A, 6B, 7A, 7B of the recorder 4'. The first interface 6A of the recorder 4' is connected to the first electrode area 2A of the first electrode 2' via a first lead 8A. The second interface 6B is connected to the second electrode area 2B of the first electrode 2' via a second lead 8B. The third interface 7A is connected to the third electrode area 3A of the second electrode 3' via a third lead 9A and the fourth interface 7B is connected to the fourth electrode area 3B of the second electrode 3' via a fourth lead 9B.

Figure 5A:
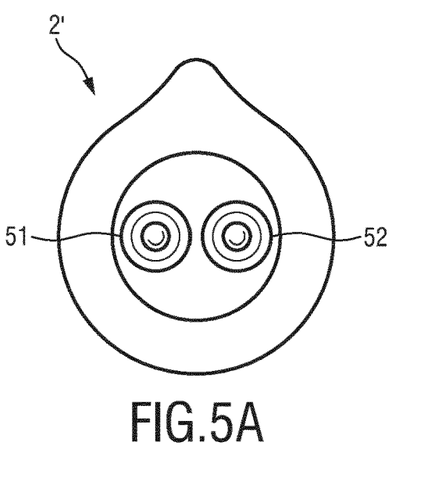
FIG. 5A shows a top view of an electrode patch according to an aspect of the present invention.
Figure 5B:
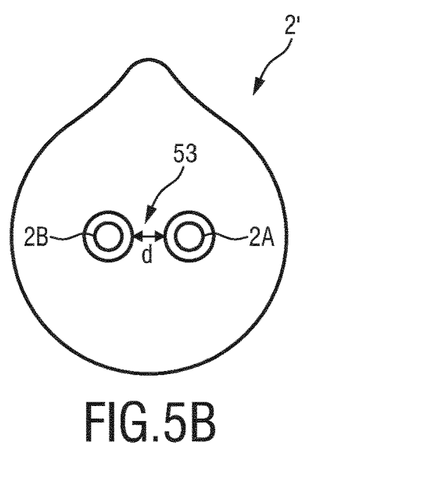
FIG. 5B shows a bottom view of an electrode patch according to an aspect of the present invention.
Figure 6:
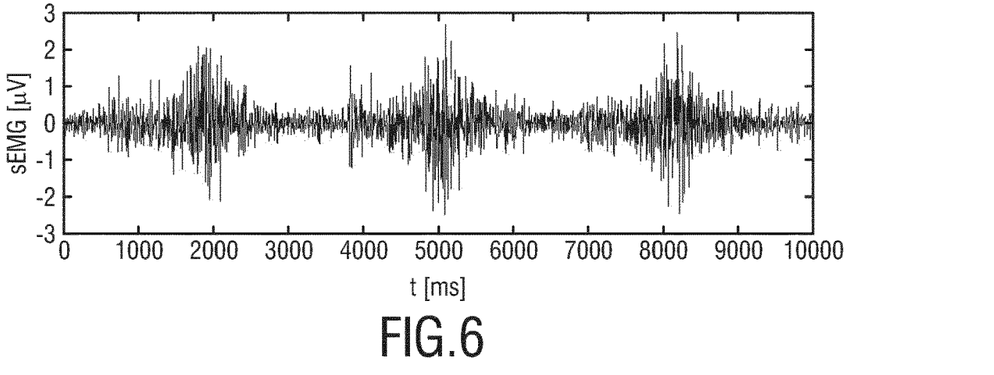
FIG. 6 shows an exemplary surface EMG recording made on the intercostal muscles of a subject.

FIGS. 5A and 5B show an exemplary embodiment of a first electrode 2' comprising a first electrode area 2A and a second electrode area 2B for separately contacting the skin of the subject 100.

It should be highlighted that in general, it is not desirable to reduce an electrode area by splitting the area of one electrode into separate electrode areas, since decreasing electrode area increases the noise, wherein the noise is proportional to $1/\sqrt{\text{electrodearea}}$.

FIG. 5A shows a top view of the first electrode 2' comprising a first connector 51 and a second connector 52. FIG. 5A thus shows the side of the electrode patch facing away from the skin of the subject during use. The first connector 51 is configured for connection to the first electrode area 2A for contacting the skin of the subject. The second connector 52 is configured for connecting the second electrode area 2B for contacting the skin of the subject.

FIG. 5B shows a bottom view of the first electrode 2'. The first electrode area 2A and the second electrode area 2B are insulated from each other. For example, the areas can be isolated by a gap 53 between the first electrode area 2A and the second electrode area 2B. The first electrode area 2A and the second electrode area 2B can also be separated by a non-conductive material. Advantageously, the first electrode area 2A and the second electrode area 2B are separated by a distance d of 3-4 mm as indicated by the arrow in FIG. 5B. When applied to the skin of the subject 100, a separation or distance d between the first electrode area 2A and the second electrode area 2B of the first electrode 2' should be smaller than a distance between the first electrode 2' and the second electrode 3'. It should further be noted that an electrode patch can comprise more than two electrode areas and that different connectors can be used.

In the embodiment shown in FIGS. 5A and 5B, the first electrode 2' is implemented as a double contact EMG wet-gel electrode patch. However, different types of electrodes and/or electrode areas may be used in the alternative. The electrode patch advantageously comprises at least two electrically insulated electrode areas with independent connection points which enable the connection of at least two separate leads to the recorder. Each contact point of the patch can have, for example, its own separate/isolated wet-gel electrolyte area. It will be appreciated that knowledge of existing single contact electrodes can be used for implementing an electrode comprising at least two separate electrically insulated electrode areas.

Figure 4:
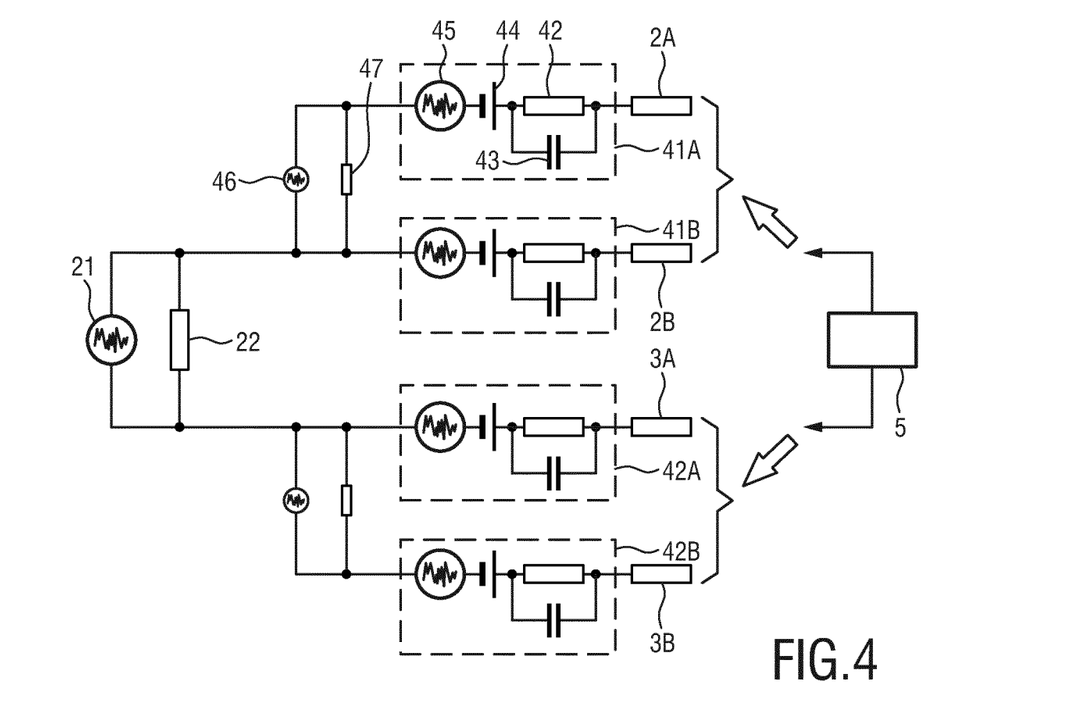
FIG. 4 shows an electrical equivalent model of the EMG setup of FIG. 3.

FIG. 4 shows a simplified electrical equivalent model of the electromyography system 1' as depicted in FIG. 3 when applied to a skin of the subject 100. The upper half of FIG. 4 essentially belongs to the first electrode 2', whereas the lower half in FIG. 4 corresponds to the second electrode 3'. As in FIG. 2, the object is measure the main wanted EMG signal 21 which is modeled in parallel to the tissue impedance 22. The crosstalk signal 23, as shown in FIG. 2, is omitted in FIG. 4 for clarity.

Figure 7:
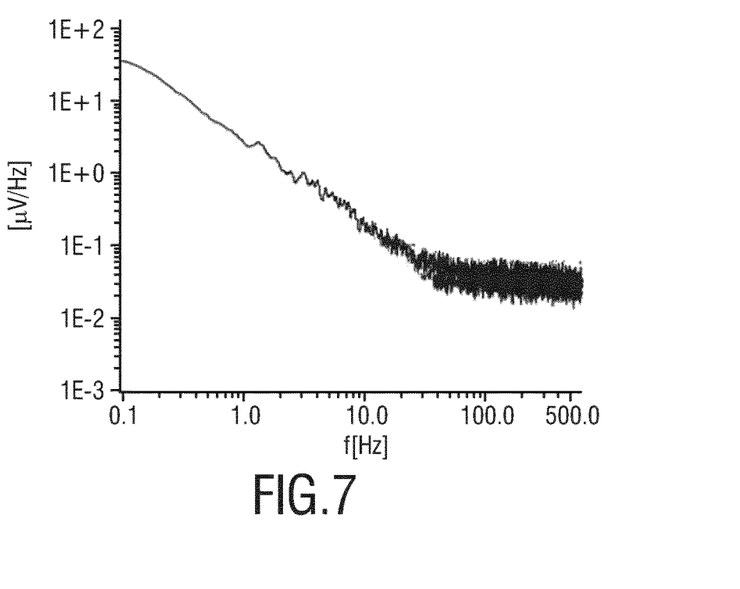
FIG. 7 shows an exemplary graph of electrode-skin excess noise.

The inventors have found that apart from crosstalk, such as intermittent interference caused by the electrical signals for example from the heart, one of the most significant sources of interference and surface EMG measurements is the noise generated in a boundary between the measuring electrodes and the skin. In particular, this noise can have a 1/f spectral characteristic, where f represents the frequency. This noise can be explained as a result of ionic charge transport through a semi-porous membrane, i.e., through a skin-electrolyte boundary in this case. An example of typical 1/f electrode noise is shown in FIG. 7. It was found that the amount and repeatability of excess noise occurring in this way are highly dependent upon the quality of the electrode-skin contact. It is therefore suggested to perform a noise measurement for determining a contact quality of an electrode-skin contact.

The electrical equivalent circuit diagram of FIG. 4 thus comprises four electrode-skin contacts which are depicted by simplified electrode-skin models 41A-42B. The first electrode 2' comprises two separate electrode-skin contacts 41A, 41B, wherein electrode-skin contact 41A corresponds to the first electrode area 2A of the first electrode and electrode-skin contact 41B corresponds to the second electrode area 2B of the first electrode. The second electrode 3' comprises two separate electrode-skin contacts 42A, 42B, wherein the electrode-skin contact 42A corresponds to the third electrode area 3A of the second electrode and the fourth electrode-skin contact 42B corresponds to the fourth electrode area 3B of the second electrode.

Each electrode-skin contact 41A-42B can be modeled as a combination of elements comprising a resistance 42 and reactance 43, which functionally acts as a first order low-pass filter, a DC voltage source 44 representing a half-cell potential of the electrode (0.222 V at 25° C. for silver/silver chloride (Ag/AgCl)). Furthermore, the electrode-skin contact can be modeled as comprising a 1/f noise source 45 caused by ionic charge transfer across the skin-electrolyte boundary. It is suggested to use this noise source in order to quantify and/or indicate a contact quality.

It should be noted that, when looking into the first electrode 2' via contacts to the first electrode area 2A and the second electrode area 2B, not only contributions from the two electrode-skin contacts 41A and 41B may be seen, but also a residual EMG signal 46 and a residual tissue impedance 47. However, in particular for a small separation between the first electrode area 2A and the second electrode area 2B, such residual contributions can be tolerated. It has been found that EMG signals generated from within the body and measured at the surface via electrodes gets small in amplitude as the spacing between the electrodes decreases. Hence, when looking into the terminals of one electrode comprising electrically insulated but closely spaced electrode areas, the noise that is measured between the first electrode area and the second electrode area of the first electrode is dominated by the series combination of the two noise sources in the electrode.

The electrode-skin contacts of the first electrode area 2A and the second electrode area 2B can thus be seen as a series combination in each electrode patch. The noise determined from this series combination can serve as an indicator for determining a contact quality of an electrode-skin contact of the first electrode.

For example, if the measured noise exceeds a predetermined threshold, the electromyography system may notify the user to reposition the electrode. A notification can be issued for example via an output unit 11 which can be optionally comprised in the recorder 4' according to the non-limiting embodiment shown in FIG. 3. Correspondingly, if a measured noise level is below a second predetermined threshold, this could indicate a short circuit between the first electrode area and the second electrode area. Hence, the electrode may again be repositioned or might have to be replaced.

Figure 8:
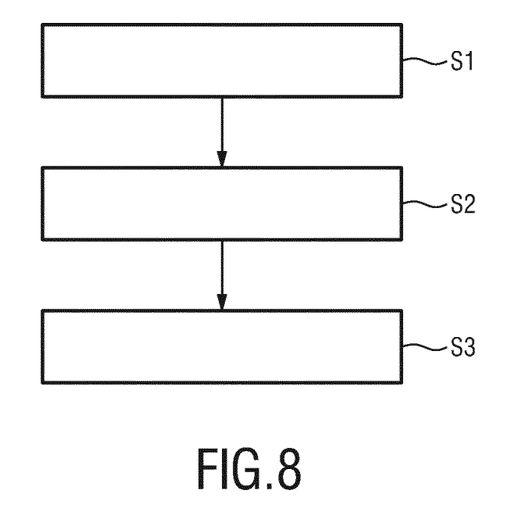
FIG. 8 shows a flow chart of a method for electromyogram measurements according to an aspect of the present invention.

FIG. 8 illustrates an exemplary embodiment of a method for electromyogram measurements according to an aspect of the present invention comprising the following steps:

In a first step S1, a first signal from a first electrode area 2A of the first electrode 2' for contacting a skin of the subject is obtained.

In a second step S2 a second signal from a second electrode area 2B of the first electrode 2' for contacting a skin of the subject as obtained, wherein this first electrode area 2A and the second electrode area 2B are insulated from each other.

In a third step S3, a noise measurement is performed between the first electrode area 2A and the second electrode area 2B of the first electrode 2' for determining a contact quality of an electrode-skin contact of the first electrode 2'.

In an optional further step, an electromyography signal can be recorded between the first electrode 2' and a further second electrode 3'. Correspondingly, a contact quality of an electrode-skin contact of the second electrode 3' can also be determined based on noise measurement as described above, provided that the second electrode 3' comprises at least a third electrode area 3A and a fourth electrode area 3B, wherein the third electrode area 3A and the fourth electrode area 3B are insulated from each other.

An exemplary sequence of measurements performed by the electromyography system 1' will be described with reference to FIGS. 9A to 9C in conjunction with FIGS. 3 and 4. A corresponding method can comprise the following steps.

Figure 9A:
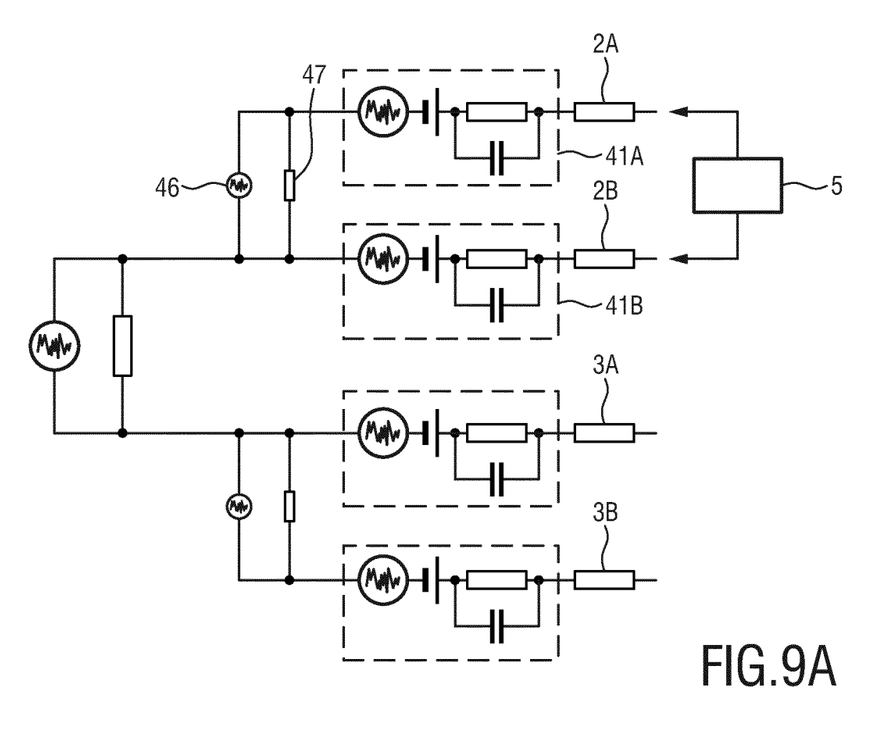
FIG. 9A shows a first measurement configuration during a first measurement step.

Referring to FIG. 9A, in a first step, a noise measurement is performed between the first electrode area 2A and the second electrode area 2B of the first electrode 2' for determining a contact quality of an electrode-skin contact of the first electrode 2'. In an embodiment, as shown in FIG. 3, the recorder 4' can comprise a switching unit 10 which establishes contact between the first interface 6A of the recorder 4' and a first input 12A of the measurement unit 5 and further establishes contact between the second interface 6B of the recorder 4' and a second input 12B of the measurement unit 5. The measurement unit 5 can thereby perform the noise measurement between the first electrode area 2A and the second electrode area 2B of the first electrode 2'. The measurement comprises a series combination of the electrode-skin contacts 41A and 41B of the first electrode area 2A and the second electrode area 2B respectively as well as the tolerably low residual EMG signal 46 and residual tissue impedance 47.

Figure 9B:
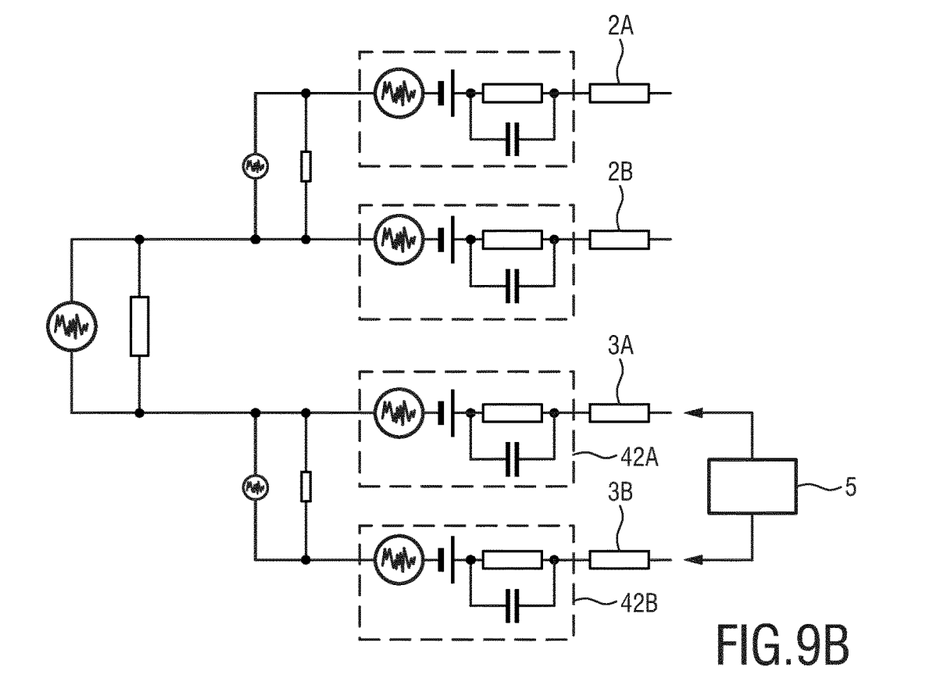
FIG. 9B shows a second measurement configuration during a second measurement step.

Referring to FIG. 9B, in a second step, a corresponding noise measurement can be performed between the third electrode area 3A and the fourth electrode area 3B of the second electrode 3' for determining a contact quality of an electrode-skin contact of the second electrode 3'. Referring to the embodiment shown in FIG. 3, the switching unit 10 can thus be configured to establish a connection between the third interface 7A of the recorder 4' and the first input 12A of the measurement unit and to establish a connection between the fourth interface 7B of the recorder 4' and the second input 12B of the measurement unit 5. The measurement unit 5 can thereby perform the noise measurement between the third electrode area 3A and the fourth electrode area 3B of the second electrode 3'. The measurement comprises a series combination of the electrode-skin contacts 42A and 42B of the third electrode area 3A and the fourth electrode area 3B respectively as well as the tolerably low residual EMG signal and residual tissue impedance. In an alternative embodiment, the measurement unit 5 can comprise additional inputs for performing the noise measurement between the first electrode area 2A and the second electrode area 2B of the first electrode 2' and the noise measurement between the third electrode area 3A and the fourth electrode area 3B of the second electrode 3' without the need for a switching unit 10. In particular, the noise measurements can then be performed in parallel.

As described with reference to FIG. 9A or FIG. 9B respectively, for each electrode patch the series combination of the respective two electrode-skin contact noise sources has been established. An actual EMG measurement between the first electrode and the second electrode can now be performed between at least one of the electrode areas 2A, 2B of the first electrode and at least one of the electrode areas 3A, 3B of the second electrode. Advantageously, the outputs of the first electrode area 2A and the second electrode area 2B of the first electrode 2' are combined together, for example using a combiner unit. Correspondingly, the outputs of the third electrode area 3A and the fourth electrode area 2B of the second electrode 3' can be combined together. Thus, the first electrode provides a combined electrode-skin contact 41 and the second electrode provides a combined electrode skin contact 42. Hence, a normal two lead EMG measurement configuration can be established for the actual EMG measurement.

When connecting two series connected noise sources, each of arbitrary value, in parallel, it is normally not possible to say what the resulting total parallel noise value will be. However, in this particular case, it has been found that when the electrode areas within a given single electrode patch are close together, it is reasonable to assume that the two noise sources, each originating from one of the two electrode areas, although uncorrelated, will be very similar in amplitude. Using this assumption, an equivalent parallel connected noise value can be calculated.

If measured noise voltages in series are $$\overline{V_s^2} = \overline{V_1^2} + \overline{V_2^2},$$

and if because of close proximity $$\overline{V_2^2} \approx \overline{V_2^2},$$

then $$\overline{V_s^2}/2 = \overline{V^2} \qquad (1)$$

where $$\overline{V^2} = \overline{V_1^2} \text{ or } \overline{V_2^2}.$$

If the noise voltages in parallel are:

$$\overline{V_p^2} = \frac{\overline{V_s^2}\,\overline{V_s^2}}{\dfrac{\overline{V_s^2}}{2} + \dfrac{\overline{V_s^2}}{2}} \qquad (2)$$

By substituting (1) in (2) the parallel noise voltage can be determined as:

$$\overline{V_p^2} = \frac{\overline{V_s^2}}{4}.$$

The total noise contribution of this parallel connected arrangement effectively represents the total noise from the first electrode 2' into the system to be measured. After performing this noise determination for the arrangement shown with reference to FIG. 9A, the same measurement can be repeated as illustrated in FIG. 9B for the second electrode 3' in the system. For each of the electrodes 2', 3' it can be indicated to a user if a sufficiently good degree of electrode-skin contact quality has been achieved. An advantage of this approach is also that a specific indication as to which of the electrodes is the problematic one can be given.

Figure 9C:
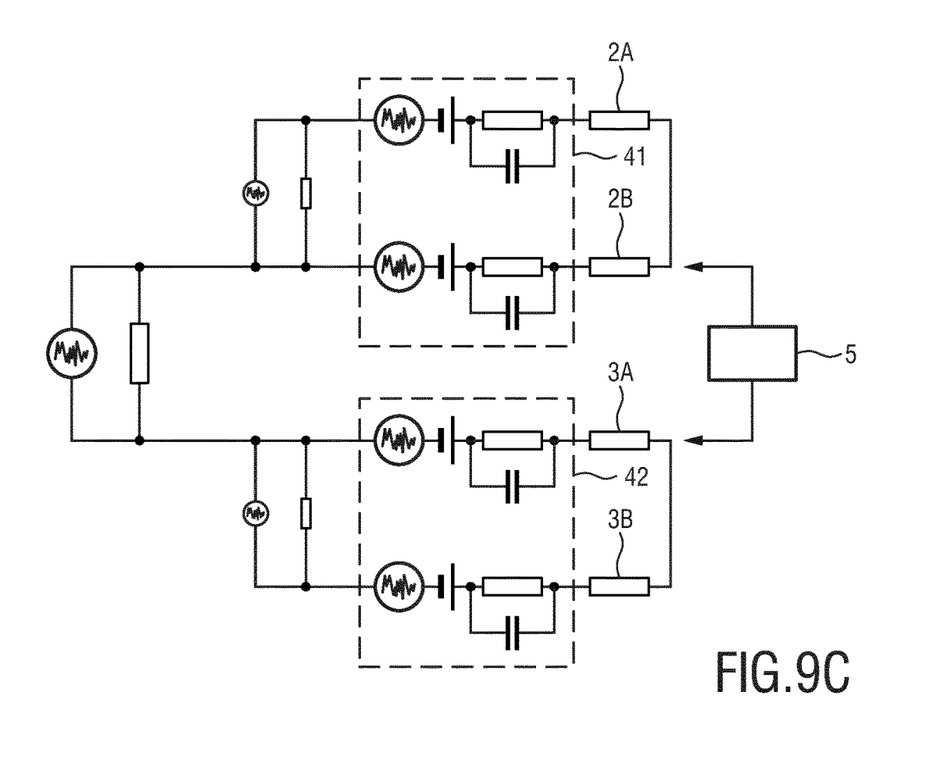
FIG. 9C shows a third measurement configuration during a third measurement step.

Referring to FIG. 9C, in a third step, an electromyogram can be recorded between the first electrode 2' and the second electrode 3'. Advantageously, the electrode areas of each electrode are short-circuited, as illustrated in FIG. 9C, in order to reduce the effect of possibly unequal noise sources in the two electrodes within a single electrode patch.

FIGS. 10 to 13 show exemplary embodiments of circuit configurations for an electromyography system according to an aspect of the present invention.

Figure 10:
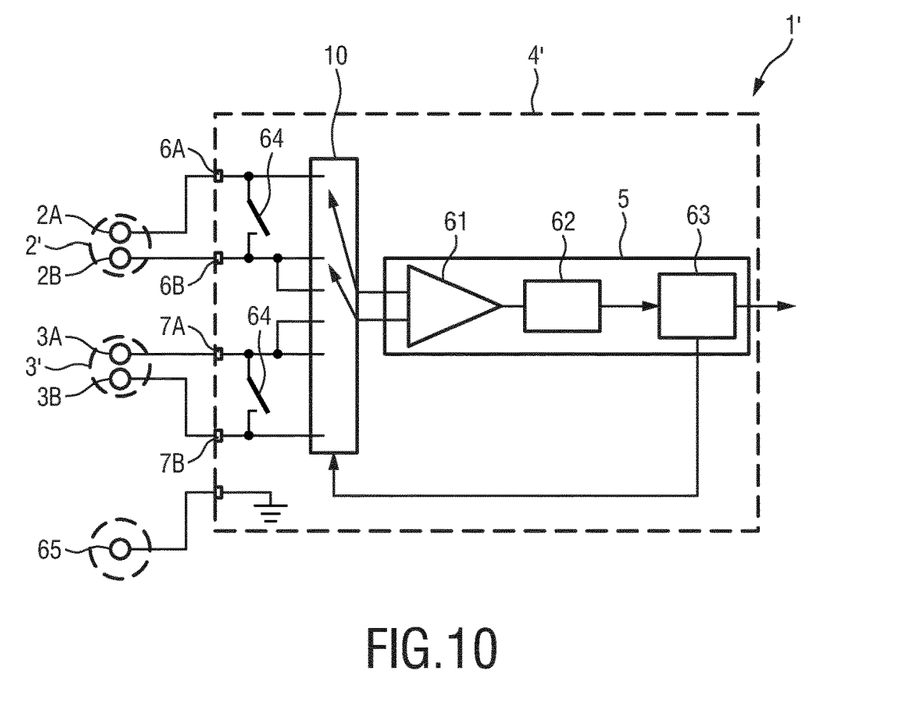
FIG. 10 shows a first exemplary circuit configuration of an electromyography system according to an aspect of the present invention.

FIG. 10 shows an electromyography system 1' comprising a first electrode 2' and a second electrode 3' for contacting a skin of the subject and a recorder 4' for recording an electromyogram between the first electrode 2' and the second electrode 3'. The first electrode 2' comprises a first electrode area 2A and a second electrode area 2B for contacting a skin of the subject, wherein the first electrode area 2A and the second electrode area 2B are insulated from each other. Correspondingly, the second electrode 3' comprises a third electrode area 3A and a fourth electrode area 3B for contacting the skin of the subject, wherein the third electrode area 3A and the fourth electrode area 3B are insulated from each other. In the shown embodiment, the recorder 4' comprises a measurement unit 5 and a switching unit 10. The measurement unit 5 comprises a differential amplifier 61, an analog-to-digital converter 62 and a microcontroller 63. It should be noted that the analog-to-digital converter 62 and/or the differential amplifier 61 can also be part of the microcontroller 63.

The switching unit 10 in this embodiment can assume three different states. In a first state, the switching unit 10 is configured to couple a signal obtained via a first interface 6A of the recorder 4' to a first input of the differential amplifier 61, and to couple a signal obtained via the second interface 6B to a second input of the differential amplifier 61. In a second state, the switching unit 10 is configured to couple a signal obtained via the third interface 7A of the recorder 4' to the first input of the differential amplifier 61 and to couple a signal obtained via the fourth interface 7B of the recorder 4' to a second input of the differential amplifier 61. In the third state, the switching unit is configured to couple a signal obtained via the first input 6A and/or to couple a signal obtained via the second interface 6B of the recorder 4' to a first input of the differential amplifier; and to couple a signal obtained via the third interface 7A and/or to couple a signal obtained via the fourth interface 7B of the recorder 4' to a second input of the differential amplifier 61. The different states of the switching unit 10 can be controlled by the microcontroller 63. The electromyography system 1' can further comprise one or more combiner units 64 for coupling outputs from different electrode areas of one electrode together, as exemplarily illustrated in FIG. 9C. Hence, the three states of the switching unit can thus be used for performing the method steps explained above with reference to FIGS. 9A to 9C.

An advantage of the embodiment shown with reference to FIG. 10 is that the same differential amplifier 61 and analog-to-digital converter 62 are used in the noise measurements (FIGS. 9A, 9B) and the subsequent actual EMG measurement such that the same noise occurring from the differential amplifier 61 and the analog-to-digital converter 62 is measured during the actual EMG measurement as in the previous calibration measurements for determining the electrode-skin contact quality based on the performed noise measurement.

The recorder 4' can further comprise an optional reference electrode 65, in particular a ground electrode, which advantageously improves a common mode rejection ratio (CMRR). Hence, an additional electrode may be used, advantageously applied to an electrical neutral place on the body, to limit excessive common mode excursions.

Figure 11:
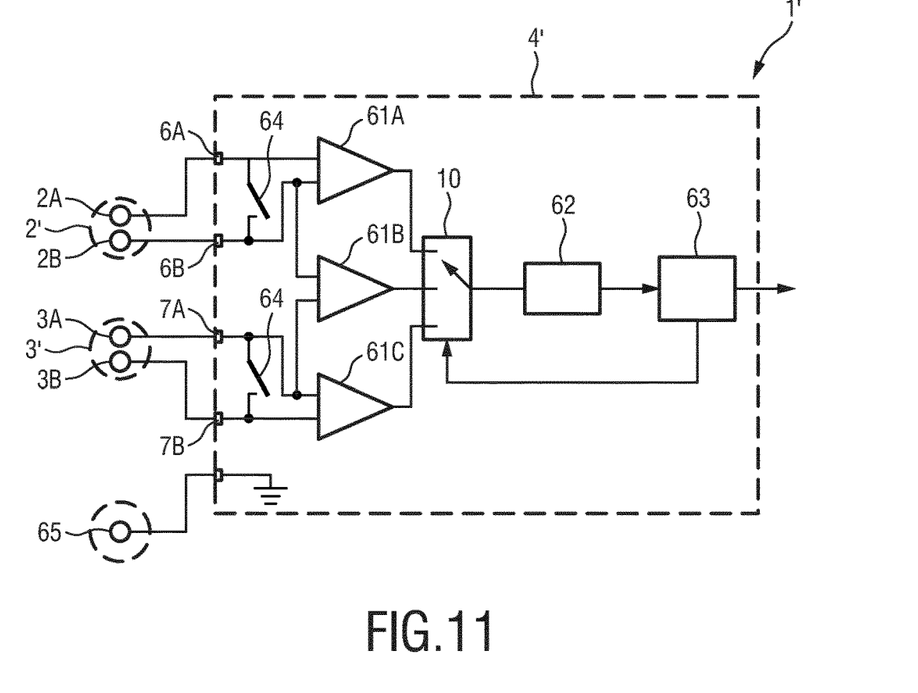
FIG. 11 shows a second exemplary circuit configuration of an electromyography system according to an aspect of the present invention.
Figure 12:
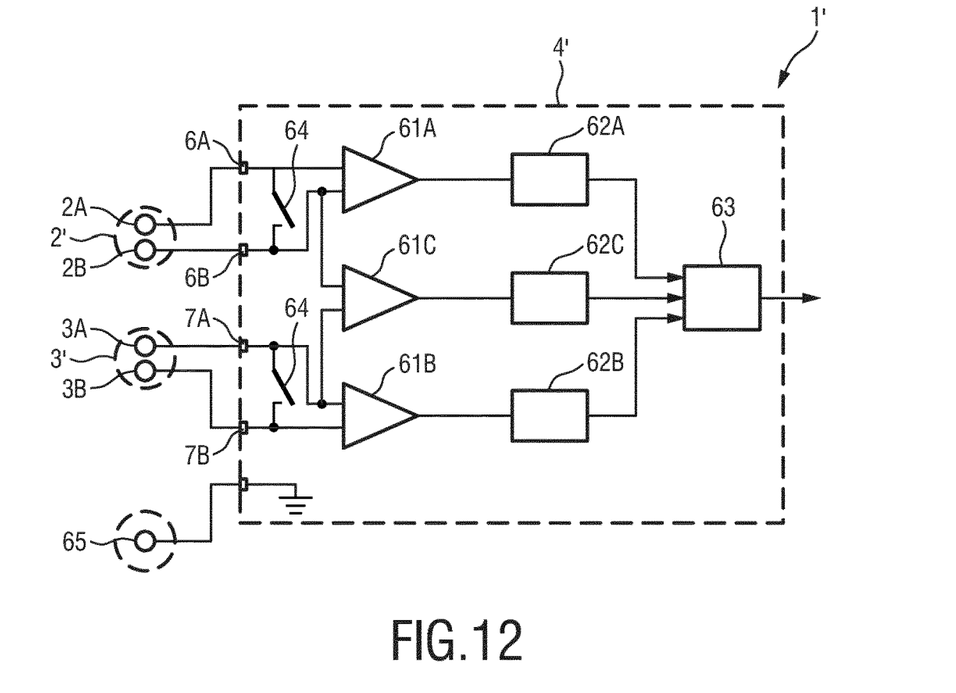
FIG. 12 shows a third exemplary circuit configuration of an electromyography system according to an aspect of the present invention.
Figure 13:
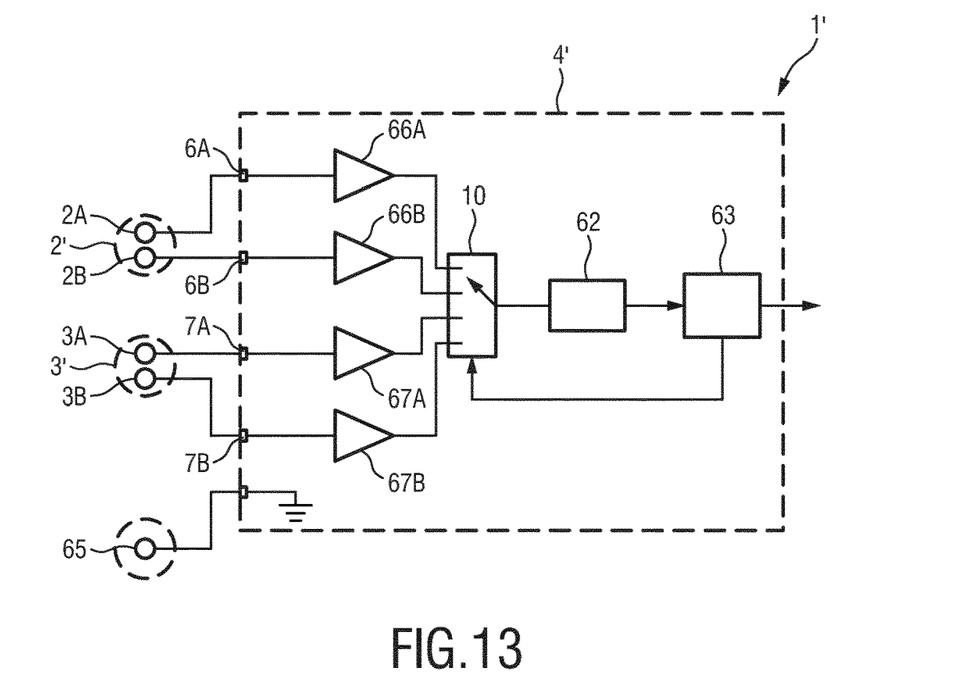
FIG. 13 shows a fourth exemplary circuit configuration of an electromyography system according to a further aspect of the present invention.

The embodiments shown in FIGS. 11 to 13 can feature similar and/or identical elements as described above. In the following, only differences to afore-mentioned embodiments will be highlighted.

Referring to FIG. 11, positions of the differential amplifier 61 and the switching unit 10 have been changed in the signal processing chain. An advantage of this embodiment is that the typically rather weak signals received from the electrodes and/or electrode areas applied to the skin of the subject are directly provided to differential amplifiers 61A to 61C, such that no switching has to be performed on these rather weak signals. The embodiment shown in FIG. 11 again includes further circuit elements as explained above with reference to FIG. 10.

FIG. 12 illustrates an embodiment without a switching unit 10. In this embodiment, a differential amplifier 61A, 61B and corresponding analog-to-digital converter 62A, 62B can be provided for each noise measurement between different areas of one electrode and an additional differential amplifier 61C and corresponding analog-to-digital converter 62C is provided for the actual EMG measurement. In this embodiment, the output of each analog-to-digital converter is provided to an input of the microcontroller 63. Alternatively, instead of using separate inputs, the digital signals provided by the respective analog-to-digital converters can also be provided to an input of the microcontroller 63 sequentially.

FIG. 13 shows a further embodiment of an electromyogram system according to an aspect of the present invention. Instead of using differential amplifiers 61, interfaces of the recorder 4' are connected to single-input amplifiers such as unipolar ramp amplifiers 66A, 66B, 67A, 67B. The outputs of these amplifiers can be provided to a switching unit 10 which selectively couples them to an analog-to-digital converter 62 and provides the output to a microcontroller 63. It should be noted that, for example, four parallel analog-to-digital converters can be used instead of the combination of switching unit 10 and analog-to-digital converter 62. Advantageously, a part of the signal processing can be transferred to the digital domain for signal processing in the microcontroller 63. For example, the noise measurement between the first electrode area 2A and the second electrode area 2B can be effected by taking the difference of the signals received from the amplifiers 66A and 66B for determining a contact quality of an electrode-skin contact of the first electrode 2'. Correspondingly, a difference of the output signals of the amplifiers 67A and 67B can be used to perform a noise measurement between the third electrode area 3A and a fourth electrode area 3B of the second electrode for determining a contact quality of an electrode-skin contact of the second electrode 3'. In this embodiment, the optional combiner unit 64 can be implemented by connecting the outputs from the first electrode area 2A and the second electrode area 2B electrically or by summing up signals received from the amplifiers 66A and 66B in the digital domain. A corresponding operation can be performed for the third electrode area 3A and the fourth electrode area 3B of the second electrode. An advantage of this embodiment is that noise measurement as well as an actual measurement of the EMG signal can be performed in parallel. In other words, a determination of the skin-electrode contact quality can be performed during the actual measurement.

In conclusion, an electromyography system, electromyogram recorder and method for electromyogram measurements have been presented which enable detection of poor quality contact between electrode and skin. Hence, an untrained person can take reliable measurements. This is particularly advantageous in a home healthcare setup where trained personnel are not constantly available.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage. It should be noted that optionally more than two electrodes can be provided for the EMG measurement. An electrode can optionally comprise more than two electrically insulated electrode areas.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Electromyography system comprising:
a first electrode and a second electrode configured to contact a skin of a subject, and a recorder for recording an electromyogram between the first electrode and the second electrode;
wherein the first electrode comprises a first electrode area and a second electrode area configured to contact the skin of the subject, wherein the first electrode area and the second electrode area are insulated from each other;
the recorder is configured to perform a noise measurement between the first electrode area and the second electrode area of the first electrode and configured to determine a contact quality of an electrode-skin contact of the first electrode based on the noise measurement between the first electrode area and the second electrode area, and wherein the recorder includes an output unit configured to output a notification to reposition the first electrode when the noise measurement between the first electrode area and the second electrode area exceeds a predetermined threshold; and further comprising a switching unit for selectively connecting the first electrode area and the second electrode area to a measurement unit of the recorder for performing the noise measurement; or the first electrode and the second electrode to the measurement unit of the recorder for recording the electromyogram.

2. Electromyography system according to claim 1, wherein the second electrode comprises a third electrode area and a fourth electrode area configured to contact the skin of the subject; wherein the third electrode area and the fourth electrode area are insulated from each other; and the recorder is further configured to also perform a noise measurement between the third electrode area and the fourth electrode area of the second electrode and configured to determine a contact quality of an electrode-skin contact of the second electrode based on the noise measurement between the third electrode area and the second electrode area.

3. Electromyography system according to claim 1, further comprising a combiner unit for combining signals from the first electrode area and the second electrode area to obtain a combined signal of the first electrode.

4. Electromyography system according to claim 1, wherein the recorder is configured to determine a noise contribution of the first electrode based on the noise measurement between the first electrode area and the second electrode area of the first electrode.

5. Electromyography system according to claim 1, wherein the first electrode is comprised in an electrode patch comprising the first electrode area and the second electrode area.

6. Electromyography system according to claim 1, wherein the first electrode comprises
a first connection point electrically coupled to the first electrode area; and
a second connection point electrically coupled to the second electrode area.

7. Electromyography system according to claim 1, wherein at least one of the electrodes is a wet gel electrode and/or at least one of the electrode areas is a wet gel electrode area.

8. Electromyography system according to claim 1, wherein the first electrode area and the second electrode area are separated by a distance of 3 to 4 millimeters.

9. Electromyography system according to claim 1, further comprising a reference electrode.

10. Electromyogram recorder for recording
an electromyography signal between a first electrode and a second electrode, the recorder comprising:
a first interface for obtaining a first signal from a first electrode area of the first electrode configured to contact a skin of a subject;
a second interface for obtaining a second signal from a second electrode area of the first electrode, wherein the first electrode area and the second electrode area are insulated from each other;
wherein the recorder is configured to perform a noise measurement between the first electrode area and the second electrode area of the first electrode and configured to determine a contact quality of an electrode-skin contact of the first electrode based on the noise measurement between the first electrode area and the second electrode area, and wherein the recorder includes an output unit configured to output a notification to reposition the first electrode when the noise measurement between the first electrode area and the second electrode area exceeds a predetermined threshold; and further comprising a switching unit for selectively connecting the first electrode area and the second electrode area to a measurement unit of the recorder for performing the noise measurement; or
the first electrode and the second electrode to the measurement unit of the recorder for recording the electromyogram.

11. Method for electromyogram measurements comprising the steps of:
obtaining a first signal from a first electrode area of a first electrode configured to contact a skin of a subject;
obtaining a second signal from a second electrode area of the first electrode, wherein the first electrode area and the second electrode area are insulated from each other;
performing a noise measurement between the first electrode area and the second electrode area of the first electrode and determining a contact quality of an electrode-skin contact of the first electrode based on the noise measurement between the first electrode area and the second electrode area;
outputting a notification to reposition the first electrode when the noise measurement between the first electrode area and the second electrode area exceeds a predetermined threshold;
recording an electromyography signal between the first electrode and a second electrode; and further comprising a switching unit for selectively connecting the first electrode area and the second electrode area to a measurement unit of the recorder for performing the noise measurement; or
the first electrode and the second electrode to the measurement unit of the recorder for recording the electromyogram.

12. Computer program comprising program code means for causing a computer to carry out the steps of the method as claimed in claim 11 when said computer program is carried out on a computer.

13. Electromyography system according to claim 1, wherein the first electrode area and the second electrode area are composed of the same material.

* * * * *